United States Patent
Mupende et al.

(10) Patent No.: US 9,873,597 B2
(45) Date of Patent: Jan. 23, 2018

(54) DEVICE FOR DETECTING THE REPLACEMENT STATE OF WEAR OF A HIGH-STRENGTH FIBER ROPE DURING USE IN LIFTING GEAR

(71) Applicant: Liebherr-Components Biberach GmbH, Biberach an der Riss (DE)

(72) Inventors: Ilaka Mupende, Neu-Ulm (DE); Horst Zerza, Biberach an der Riss (DE)

(73) Assignee: Liebherr-Components Biberach GmbH, Biberach an der Riss (DE)

( * ) Notice: Subject to any disclaimer, the term of this patent is extended or adjusted under 35 U.S.C. 154(b) by 138 days.

(21) Appl. No.: 14/915,622

(22) PCT Filed: Aug. 14, 2014

(86) PCT No.: PCT/EP2014/002245
§ 371 (c)(1),
(2) Date: Feb. 29, 2016

(87) PCT Pub. No.: WO2015/028126
PCT Pub. Date: Mar. 5, 2015

(65) Prior Publication Data
US 2016/0221800 A1    Aug. 4, 2016

(30) Foreign Application Priority Data

Aug. 28, 2013 (DE) .................. 10 2013 014 349
Oct. 15, 2013 (DE) .................. 10 2013 017 110

(51) Int. Cl.
*B66C 15/06* (2006.01)
*B66C 15/00* (2006.01)
(Continued)

(52) U.S. Cl.
CPC .............. *B66C 15/06* (2013.01); *B66C 15/00* (2013.01); *B66D 1/54* (2013.01); *G01N 3/22* (2013.01);
(Continued)

(58) Field of Classification Search
USPC ............................................ 212/271; 73/854
See application file for complete search history.

(56) References Cited

U.S. PATENT DOCUMENTS 3,664,182 A * 5/1972 Butler ...................... G01N 3/22
                                                        73/794
6,247,359 B1    6/2001 De Angelis
2014/0027401 A1 1/2014 Ilaka et al.

FOREIGN PATENT DOCUMENTS

DE        218177 A1    1/1985
DE     19956265 B4    6/2005
(Continued)

OTHER PUBLICATIONS

State Intellectual Property Office of the People's Republic of China, Office Action and Search Report Issued in Application No. 201480058972.4, dated Apr. 25, 2017, 16 pages. (Submitted with Partial Translation).
(Continued)

*Primary Examiner* — Laura Martin
*Assistant Examiner* — Jean Morello
(74) *Attorney, Agent, or Firm* — McCoy Russell LLP

(57) ABSTRACT

The present invention relates generally to hoists such as cranes which instead of steel wire ropes use high-strength fiber ropes. The invention relates in particular to an arrangement for detecting the discard state of a high-strength fiber rope when used on such hoists, with a means for detecting at least one rope parameter and an evaluation unit for evaluating the rope parameter, and providing a discard
(Continued)

signal depending upon the evaluation of the rope parameters. According to the invention, the detection means comprises torsional stiffness detection means to determine the torsional stiffness of the rope, whereby the evaluation unit provides the discard signal depending on the determined torsional stiffness of the rope.

15 Claims, 2 Drawing Sheets

(51) Int. Cl.
    *B66D 1/54*       (2006.01)
    *G01N 3/22*       (2006.01)
    *G01N 3/56*       (2006.01)

(52) U.S. Cl.
    CPC .......... *G01N 3/56* (2013.01); *G01N 2203/028* (2013.01)

(56) References Cited

FOREIGN PATENT DOCUMENTS

| | | |
|---|---|---|
| DE | 202011001846 U1 | 6/2012 |
| EP | 1930496 A3 | 6/2009 |
| JP | S58160841 A | 9/1983 |
| JP | H02056391 A | 2/1990 |
| JP | H09178611 A | 7/1997 |
| JP | 2000170082 A | 6/2000 |
| JP | 2001192183 A | 7/2001 |
| WO | 2012100938 A1 | 8/2012 |

OTHER PUBLICATIONS

ISA European Patent Office, International Search Report Issued in Application No. PCT/EP2014/002245, dated Nov. 5, 2014, WIPO, 5 pages.

* cited by examiner

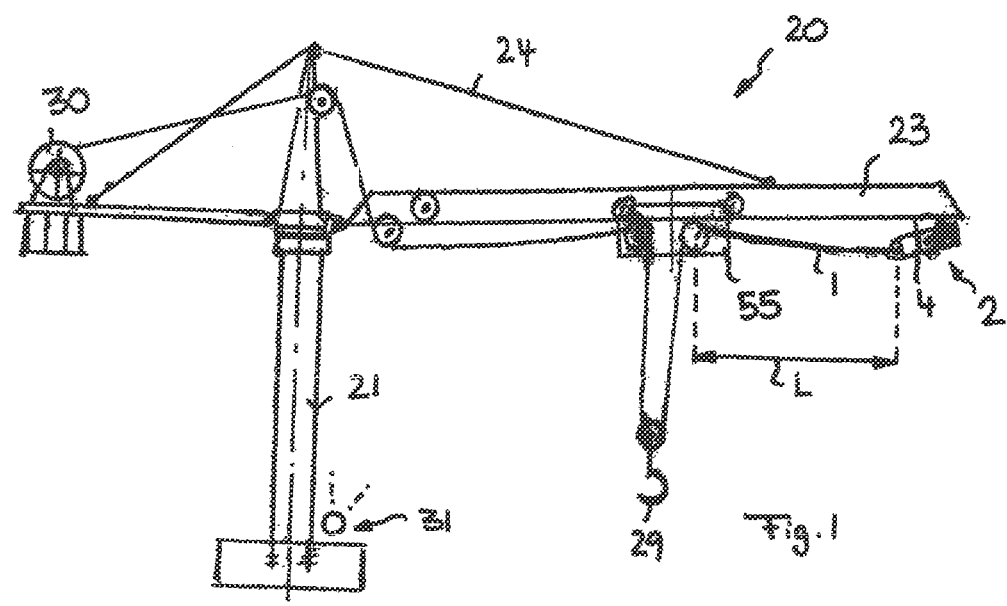
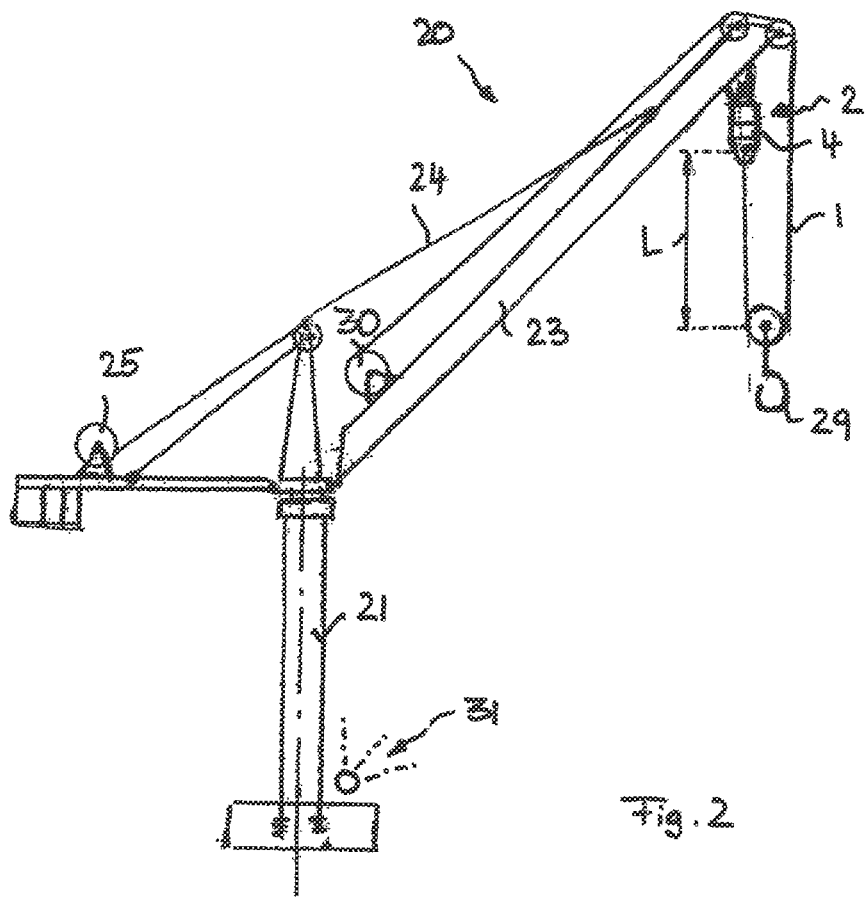

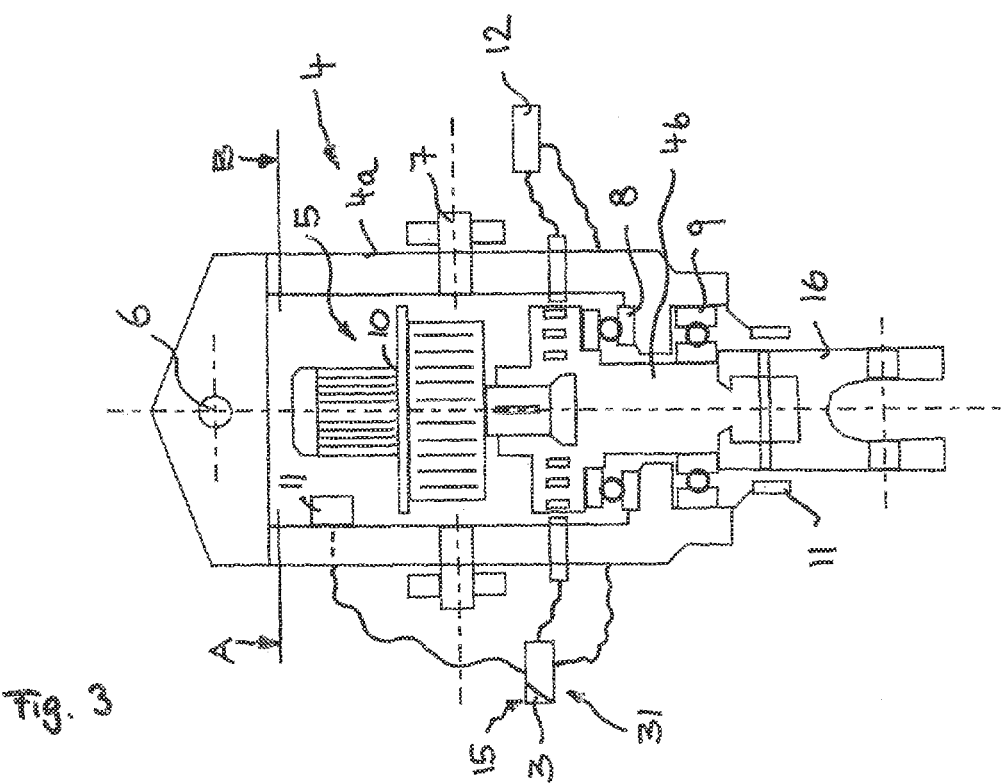

DEVICE FOR DETECTING THE REPLACEMENT STATE OF WEAR OF A HIGH-STRENGTH FIBER ROPE DURING USE IN LIFTING GEAR

CROSS REFERENCE TO RELATED APPLICATIONS

The present application is a U.S. National Phase of International Patent Application Serial No. PCT/EP2014/002245, entitled "Device for Detecting the Replacement State of Wear of a High-Strength Fibre Rope During Use in Lifting Gear," filed on Aug. 14, 2014, which claims priority to German Patent Application No. 10 2013 017 110.5, filed on Oct. 15, 2013, and to German Patent Application No. 10 2013 014 349.7, filed Aug. 28, 2013, the entire contents of each of which are hereby incorporated by reference in their entirety for all purposes.

TECHNICAL FIELD

The present invention relates generally to hoists such as cranes which instead of steel wire ropes use high-strength fiber ropes. The invention relates in particular to an arrangement for detecting the discard state of a high-strength fiber rope when used on such hoists, with a means for detecting at least one rope parameter and an evaluation unit for evaluating the rope parameter, and providing a discard signal depending upon the evaluation of the rope parameters.

BACKGROUND AND SUMMARY

Instead of steel wire ropes that have been used successfully on cranes for many years, it is recently being tried to use high-strength fiber ropes made of synthetic fibers such as aramid fibers (HMPA), aramid/carbon composites, highly modular polyethylene fibers (HMPE) or poly(p-phenylene.2,6-benzobisoxazole) fibers (PBO). The advantage of such high-strength fiber ropes is their low weight. At equal rope diameters and equal or higher tensile strengths, such high-strength fiber ropes are clearly lighter in weight than comparable steel wire ropes. In particular for high cranes with accordingly long rope lengths, this results in a major weight reduction reflected in the dead weight of the crane leading to higher payloads for an otherwise unchanged crane design.

However, a disadvantage of such high-strength fiber ropes is their breaking behavior, i.e. their failure without any distinct long-term prior warning. While wear is clearly indicated with steel wire ropes, showing failure long in advance, for example when individual steel wires break and splice open, which is easily detected, high-strength fibers show few signs of excess splicing that could be detected with the naked eye and that would show long before their actual failure. They therefore require intelligent monitoring measures to allow the early detection of when the discard state of high-strength fiber ropes will occur.

It is known from WO 2012/100938 A1 to detect the discard state of a high-strength fiber rope by testing various rope discard criteria which change over the time in which a rope is used and under stress. Here, the rope diameter, the shear stress stiffness measured by the cross-sectional changes resulting when the rope is pinched, and by the number of completed stress cycles. However, the informative value of these individual discard criteria is limited, which means that the interaction of these discard criteria must be monitored and evaluated in a rather complex monitoring process before the discard state can actually be detected with reliability.

Based on this, it is the object of the present invention to provide an improved device for detecting the discard state of high-strength fiber ropes which avoids the disadvantages of the prior art and advantageously develops it further. Preferably, a simple but reliable and precise detection of the discard state is to be achieved which economically utilizes the remaining service life if the fiber rope without jeopardizing safety, and which can be used on construction machinery with simple detection means functioning reliably even under heavy-duty working conditions.

According to the invention, the above object is achieved with a device according to the present application.

It is therefore suggested to monitor the rope's torsional stiffness and to determine the discard state by means of the rope's torsional stiffness. The rope's torsional stiffness means the rope's resistance or moment of resistance against the rope being twisted. It takes a certain torque to twist the end sections of a rope sector lengthwise relative to each other, i.e. to chordate or twist the rope, to achieve the above twist whereby the said torque depends on the rope's stiffness. According to the invention, the detection means comprises torsional stiffness determination means for determining the rope's torsional stiffness, whereby the evaluation unit provides the discard signal depending on the rope's determined torsional stiffness. While steel wire ropes do not show significant changes in torsional stiffness depending on the rope's service life, this is different with high-strength fiber ropes. The filaments which are still flexible at the beginning of the rope's use, are made harder and the rope is made stiffer by the tensile stress and the bending stress. This increase in the rope's torsional stiffness is easy to measure, which means that the discard state can be determined reliably and precisely by the rope's monitored torsional stiffness. It shows that rope twisting tests with a new rope show a rather low torsional stiffness while ropes driven to the breaking point show a very high torsional stiffness in the end due to prolonged and severe stress, namely many times that of the rope's original state. This increase rises continuously with the cycles-to-failure rate, reaching the highest point when the rope breaks, which means that the evaluation unit can determine the discard state relatively easily.

In the further development of the invention, the torsional stiffness determination means can comprise a swivel that can be integrated in the rope drive or used to sling the rope. Sometimes such a swivel is also called the rope swivel; it usually consists of two swivel parts which can be twisted relative to each other in the rope's lengthwise direction, especially about a rotational axis coaxially to the rope's longitudinal axis, whereby for example a fixed swivel part can be non-rotatably secured on a crane boom in longitudinal direction, while the rotatable swivel part is non-rotatably connected to the rope. To use such a prior-art swivel to determine the rope's torsional stiffness, a further development of the invention can provide a rotary drive for forcing the two swivel parts to rotate relative to each other, in particular this rotary drive can be integrated in an interior space of the swivel whereby the rotary drive can, for example, be an electric motor, if need be in conjunction with a gear.

The said rotary drive functionally sits between the two swivel parts and is rotationally supported in relation to the two swivel parts, i.e. in relation to a twist about the swivel axis. In particular, a drive axis of the rotary drive, for example a gear output shaft, can be connected with the rotatable swivel part on which the rope is non-rotatably secured, while a motor housing is non-rotatably connected with the non-rotatable swivel part or at least with only limited rotatability.

In a further development of the invention, the swivel can be provided with a torque meter and/or twist angle meter or torsion angle meter to determine the torque applied when the swivel is forced to rotate or to record or determine the twist angle of the two swivel parts relative to each other when the swivel is forced to rotate.

In principle, the said torque meters or torque angle meters can be of various designs. For example, in a further development of the invention, the torque meter can be integrated in the rotary drive, for example when an electric motor is used, it can record its electrical control variables such as currency and voltage to determine the thus generated torque. As an alternative or in addition to such a drive parameter meter, the torque meter can also determine the reaction moment induced by the fixed swivel part in its holding member, for example in the form of a crane boom. As an alternative or in addition to that, the torque meter can also be installed in the drive gear or the rotatable swivel part, for example between the drive gear and the rotatable swivel part, for example in the form of a torsion measurement socket or such.

In principle, the torsion angle meter or twist meter can also be of various designs, for example integrated into the drive gear or its drive motor. As an alternative or in addition, the twist meter can directly record the twist of the two swivel parts relative to each other.

The rope's torsional stiffness can be detected by the torsional stiffness detection means by means of a twist of the rope achieved by a predetermined torque and/r by means of the torque required for a predetermined twist. In a further development of the invention, these two detection criteria can also be used in combination with each other, in particular such that it is determined which force is required for a predetermined twist and which twist occurs with a predetermined torque, to take into consideration the non-linearity that may result with torsional stiffness.

To avoid distorting or influencing the measuring of the rope's torsional stiffness by the stress of tensile forces upon the rope, the torsional stiffness determination means comprises a tensile stress adjuster which sets the same tensile force conditions on the rope for the repeating detection of the rope's torsional stiffness. In particular, the said tensile stress adjuster can comprise a tensile stress release means which essentially completely releases the rope of tensile forces when the rope's torsional stiffness is determined.

The said tensile release means can be of various designs. In an advantageous embodiment of the invention, the tensile release means can comprise holding means to hold the rope in lengthwise direction, preferably at least one rope clamp for clamping the rope, in particular for catching hoist loads on the lifting hook and the rope section to be tested for the rope's torsional stiffness, whereby the said holding means can for example be provided on the trolley of a tower crane, to relieve the rope section between the trolley and the swivel. Preferably, the test of the rope's torsional stiffness test can be conducted without a load on the lifting hook, whereby the lifting hook is preferably moved to a predetermined height by control device or manually to achieve a predetermined tensile force of the rope through the rope's dead weight and to have a certain rope length for testing.

In an advantageous further development of the invention, the torsional stiffness determination means comprises a swivel compensator which prior to conducting the test of the rope's torsional stiffness eliminates or at least greatly reduces any twist that might be present on the rope. Normally, ropes twist which are coiled on rope drums or run around rope pulleys. To avoid the distortion of the rope's torsional stiffness measurements, preferably such twist can be removed prior to the torsional stiffness test being conducted. Preferably, the said swivel compensator can also be integrated in or associated with the above described swivel. For example, the swivel compensator can comprise a rotational direction sensor which helps to determine the rotational direction or effective direction of the rope's twist, which means that the rotary drive can be activated depending on an associated rotational direction signal to turn the rope via the swivel or its rotatable swivel part in the intended rotational direction. If need be, the height of the torque at the swivel induced by the rope's twist can be determined by a torque sensor of the above described kind to activate the rotary drive for as long as the detected or determined torque induced by the rope's twist approaches zero before the torsional stiffness test is begun.

In principle, the evaluation arrangement for providing a discard signal can work in various ways, for example by monitoring changes occurring in the rope's torsional stiffness and/or by monitoring absolute values of the torsional stiffness. In particular, the said evaluation unit can be designed such that a discard signal is provided when the rope's torsional stiffness and/or its change reaches an associated threshold value.

For example, one or more reference measurements can be conducted with a new rope such that the percentage change in a rope's torsional stiffness occurring in operation can be compared with a threshold value for change, and if this value is exceeded or approached, the discard signal is provided. In particular, the discard signal can be provided when the rope's torsional stiffness increases beyond a still tolerable threshold value. As an alternative or in addition, the monitored and in operation constantly or cyclically detected torsional stiffness of a rope can be compared with an absolute threshold value predetermined by the manufacturer for a certain type of rope or a specific rope, and to provide the discard signal when this threshold value is reached or exceeded. Also as an alternative or in addition, the discard signal can be provided when the change in a rope's torsional stiffness as determined by measuring occurs to fast and/or too slowly, i.e. when the speed of change in the rope's torsional stiffness over a given time exceeds or remains below a threshold value. The speed of change over a given time can be the speed of change over the number of stress cycles recorded for example with a load cycle counter which can be taken into account by the evaluation arrangement. As an alternative or in addition, the speed of change can also only be taken into account by means of the number of measurements of the rope's torsional stiffness, for example such that discard signal is provided when the change in the rope's torsional stiffness detected after a certain number of measurements, for example after the tenth measurement, exceeds a certain predetermined threshold value.

The discard signal can simply be indicated to the crane operator, for example acoustically and/or visually, or it can be used to stop the rope drive.

In an advantageous further development of the invention, the torsional stiffness determination means can be firmly installed in the rope drive of the hoist such that the rope's torsional stiffness can be constantly monitored during operation, i.e. in the operational state of the hoist, without the necessity of having to convert the hoist into a special test modus. As an alternative or in addition, the torsional stiffness determination means can also be provided as a detachable unit that can be used in different hoists.

Below, the invention is described in more detail by means of a preferred embodiment and with reference to the drawings.

BRIEF DESCRIPTION OF FIGURES

FIG. 1 shows a schematic view of a hoist according to the invention in the form of a tower crane according to an advantageous embodiment of the invention, whose hoisting rope and/or bracing ropes can be designed for the luffable jib as fiber ropes, whereby the torsional stiffness determination means are fastened to the end of a hoist rope running from a rope drum and across a trolley at the crane's boom.

FIG. 2 shows a schematic view of a hoist according to the invention in the form of a tower crane according to another advantageous embodiment of the invention, whose boom is luffable, whereby the hoist rope running from a rope drum runs across the boom tip, and the torsional stiffness determination means are fastened to the rope end at the boom end.

FIG. 3 shows a schematic view of the swivel of the torsional stiffness determination means integrated into the rope drive of the hoist rope of the crane shown in FIG. 1, in longitudinal section showing the rotary drive of the swivel.

FIG. 4 shows a cross-sectional view of the rotary drive of the swivel of the torsional stiffness determination means, showing the torque support and the torque meter facing the rotary drive.

DETAILED DESCRIPTION

FIG. 1 shows as an example a hoist according to an advantageous embodiment of the invention in the form of a top-slewing crane 20 whose tower 21 is mounted on a carriage or solid base. Linked to tower 21 in a previously known manner is a boom 23 braced by bracing 24. The said bracing 24 can be rigid, for example in the form of bracing rods, but also adjustable in the form of a rope reeving that can be changed in length via a bracing winch 25 such that the working angle of boom 23 can be changed, as shown in FIG. 2.

As shown in FIG. 1, the tower crane 20 can be provided with a trolley boom. A movable trolley is installed on the said crane in operating position, in particular on its horizontally oriented boom 23, whereby the said trolley 55 can, for example, be moved via a trolley rope which can be guided via deflection pulleys at the boom tip.

The tower crane also comprises a hoist rope 1 that can be lowered via deflection pulleys from the boom tip where it is connected with a crane hook 29, as shown in FIG. 2, or in the version according to FIG. 1 can run via the said movable trolley 55 and deflection pulleys provided there, and can be connected with the crane hook 29. In both cases, the said hoist rope 1 runs on a hoist winch 30.

The said hoist rope 1 and/or the bracing rope can be designed as fiber ropes which can consists of synthetic fibers such as aramid fibers or fibers made from a mixture of aramid and carbon.

In both cases, the said hoist rope can be fastened to boom 23 of the crane by means of a swivel 4.

To monitor or detect the parameters of the said fiber rope relevant to its discard state, a detection means is provided that can be arranged on the crane and which together with an evaluation unit 3, which evaluates the acquired parameters, can be connected with or integrated in the electronic crane control unit 31.

As FIGS. 2 and 3 show, the torsional stiffness determination means 2 advantageously comprises the above mentioned swivel 4 shown in greater detail in FIGS. 3 and 4. The said swivel 4 comprises two swivel sections 4a and 4b which are rotatable relative to each other in the lengthwise direction of the rope. Swivel part 4a forms a fixed or non-tiltable swivel part which with regard to the rope's lengthwise direction is rigidly mounted on boom 23. It may have an oscillating, suspended or upright arrangement via a first bearing axis 6 or a lying, also oscillating arrangement via the second bearing axis 7 can be provided which allow oscillating or swivelling movements across the rope's lengthwise direction while preventing the swivel part 4 to twist in the rope's lengthwise direction.

The other swivel part 4b forms the rotatable swivel part to which the rope 1 is non-rotatably fastened. The said rotatable swivel part 4b can, for example, be rotatably mounted about the lengthwise direction of the rope via roller bearings such as in the form of an axial bearing 8 and a radial bearing 9 on the fixed swivel part 4a.

Advantageously, the rotatable swivel part 4b can be connected with a rotary drive 5 which advantageously can be located within swivel 4. For this, for example, the fixed swivel part 4a can be bell-shaped or sleeve-shaped to create accommodation for rotary drive 5. However, a reverse arrangement with bell-shaped or sleeve-shaped contours for the rotatable swivel part 4b, which then could also enclose the fixed swivel part 4a, could also be provided.

For example, the said rotary drive 5 can comprise an electric motor connected via a gear or directly non-rotatably via an output shaft with the rotatable swivel part 4b. A drive housing 10 of the rotary drive 5 can be secured against twist on the fixed swivel part 4a, for example by means of one or more torque supports 14 which can be supported via stops or other suitable bearing contours on swivel part 4a; see FIG. 4.

As FIGS. 3 and 4 show, the swivel 4 is provided with measuring means beyond the said rotary drive 5 to measure the angle of twist of the two swivel parts 4a and 4b at a rotation relative to each other as well as the torque necessary for a twist of the two swivel parts 4a and 4b and also the rotational direction. In principle, the torsion angle meter 12, torque meter 11 and rotation direction meter 13 provided for this can be of various designs and may, for example, comprise a means to measure the operating parameters of the motor for the rotary drive 5. For example, the torque can be determined from the operating parameters current and voltage of the drive motor. As an alternative or in addition, the torque meter 11 can be assigned to the said torque support 14 or rotary drive 5 against swivel part 4a to measure the torque and make it available to control device 15. The said rotation direction meter 13 can also be assigned to the torque support 14, for example combined with the said torque meter 11 into a measuring unit which measures the pressure of the torque support against the stop contour on swivel part 4a.

As an alternative or in addition, the torque meter 11 and/or the rotational direction meter 13 can also be integrated in a connector part 16 with which rope 1 is connected to the rotatable swivel part 4b.

The torsion angle meter 12 or an equivalent rev sensor can, for example, be connected to an interface between the two swivel parts 4a and 4b to directly measure the twist of the two swivel parts relative to each other. As an alternative or in addition, a torsion angle meter 12 can be assigned to rotary drive 5 or on a gear shaft or output shaft of rotary drive 5.

Advantageously, the torsional stiffness of rope 1 can be detected by means of the following steps:

First, the rope is moved into the position to be measured, for which the hoist position measuring means of the lifting hook can be used. In particular, the lifting hook is moved to a certain hoist height, and if need be, the trolley is moved into a certain position, or the boom is moved into a certain luffing position, When a new rope is used for the first time, the torsional stiffness of rope 1 is measured in the zero state as a reference base for further measurements. For this, the determined test length L of the rope can be set at a certain value and stored, for example by bringing the lifting hook to a certain hoist height, the trolley to a certain position and/or the boom into a certain luffing position. This can be measured via suitable positioning or position sensors and stored such that the reference rope length L can be set again as desired for later measurements. As FIG. 1 shows, in a tower crane with trolley, the measured rope section and its length L can be between swivel 4 and the deflection pulley of the trolley. In a tower crane with luffable boom 23, the rope section and its length L can be between the said swivel and the lifting hook or the lifting hook sheath.

Preferable, the test can be done at the hook without a load such that the rope always has the same pull for all subsequent tests.

To begin a torsional stiffness test, the twist existing in rope 1 must first be compensated for as much as possible. For this, the torque induced by the rope's twist into swivel 4 must be measured, which can be done with the above described torque meter 11. Then the control unit 15 controls rotary drive 5 depending on the determined torque and its direction, such that the torque induced by the rope's twist goes toward zero. That is the initial point for the actual torsional stiffness test.

Now, in the said section L of rope 1 a predetermined number of rotations is induced, and the resulting torque is measured. For that, rotary drive 5 is activated, and the toque required for the twist is measured.

As an alternative or in addition, the rotary drive can be controlled by control unit 15 such that a certain torque is induced into rope 1, whereby the resulting rotational speed or the resulting angle of twist is measured with the torsion angle meter.

The rope's torsional stiffness is determined from the measured torques and twist angles. With a fixed rotational speed, the torque required for this can be used directly as the measure of torsional stiffness, while with a fixed torque, the resulting rotational speed or the resulting angle of rotation can be used as the measure of torsional stiffness. In particular, the said measuring values of torque and angle of rotation are stored in the memory of the control unit 15 to be used as a reference base for subsequent measuring.

In predetermined time intervals—if need be in the form of a predetermined number of load cycles or bending cycles that can be recorded by a load cycle counter—the torsional stiffness is again measured as described and the results are compared with those of previous measurings, in particular with those of the new rope.

Evaluation arrangement 3 evaluates in particular—in the manner as described above—whether the rope's torsional stiffness and/or its change in relation to the new rope exceeds a predetermined threshold value.

The maximum permissible threshold value of torsional stiffness or of permissible change in the evaluation of a new rope for safe crane operation can be recorded in control unit 15 and used as a comparative basis when measuring the torsional stiffness. In a further development of the invention, a prior warning can be given when the said threshold value is approached, thus indicating that the rope should be replaced. When the said threshold value is disregarded, reached or exceeded, control unit 15 can use the discard signal generated by evaluation unit 3 to automatically shut down the operation with that rope.

Moving the rope section for determining torsional stiffness can be automatically or manually programmed.

The invention claimed is:

1. An arrangement for detecting a discard state of a high-strength fiber rope used on hoists, comprising: a detecting device to detect at least one rope parameter and an evaluation unit for evaluating the at least one rope parameter and providing a discard signal depending on the evaluation of the rope parameter, wherein the evaluation unit comprises a torsional stiffness determination device for determining the torsional stiffness of the rope, and that the evaluation unit provides the discard signal depending on the determined torsional stiffness of the rope.

2. The arrangement according claim 1, wherein the torsional stiffness determination device comprises a rotary drive for twisting a rope section about a predetermined angle of rotation and/or with a predetermined torque, and a detection device for detecting the torque and/or the angle of rotation that results from the twisting of the rope section, whereby the evaluation unit determines the rope's torsional stiffness depending on the determined torque and/or the determined angle of rotation of the rope section.

3. The arrangement according claim 2, wherein the torsional stiffness determination device comprises a swivel with a first swivel part and a second swivel part which can be twisted in relation to each other in a lengthwise rope direction and which can be forced by the rotary drive to twist in relation to each other.

4. The arrangement according to claim 3, wherein the swivel is non-rotatably connected with a rope end and is non-rotatably fastened to a base part.

5. The arrangement according to claim 3, wherein the swivel is provided with a torque meter and/or a torsion angle meter, wherein the rope's torsional stiffness can be determined with the torsional stiffness determination device from a twist that can be achieved with a predetermined torque and/or with a torque required for a predetermined twist.

6. The arrangement according to claim 3, wherein the rotary drive is integrated in an interior space enclosed by the first swivel part.

7. The arrangement according to claim 5, wherein a swivel compensator is provided to compensate for a rope twist that may be present before the rope's torsional stiffness is determined.

8. The arrangement according to claim 7, wherein the swivel compensator comprises a control component for controlling the rotary drive depending on a torque determined by the torque meter on the swivel and/or depending on a rotation direction determined by a rotation direction meter of a rope twist from the rope acting on the swivel, whereby the control component is designed such that the rotary drive can be activated such that the torque measured by the torque meter is approaching zero.

9. The arrangement according to claim 8, wherein the torque meter and/or the torsion angle meter and/or the rotation direction meter are integrated in the swivel and/or the rotary drive.

10. The arrangement according to claim 1, wherein the torsional stiffness determination device comprises a tension adjustment unit for automatically adjusting a predetermined tensile force in the rope and/or a length adjustment unit for adjusting a predetermined length of the rope section to be subjected to a torsional stiffness test.

11. The arrangement according to claim 1, wherein the evaluation unit provides the discard signal when the rope's torsional stiffness determined by the torsional stiffness determination device and/or its change exceeds a designated threshold value.

12. The arrangement according to claim 1, wherein the hoist is the hoist of a crane.

13. A crane with an arrangement for detecting a discard state of a high-strength fiber rope used on hoists, comprising: a detecting device to detect at least one rope parameter and an evaluation unit for evaluating the at least one rope parameter and providing a discard signal depending on the evaluation of the rope parameter, wherein the evaluation unit comprises a torsional stiffness determination device for determining the torsional stiffness of the rope, and wherein the evaluation unit provides the discard signal depending on the determined torsional stiffness of the rope.

14. The crane according to claim 13, wherein the torsional stiffness determination device is rigidly installed and assigned to a rope drive of the crane or designed as a removable unit such that the rope's torsional stiffness can be detected in a crane equipped for crane operation.

15. The crane according to claim 13, wherein the crane is one of a tower crane, a mobile crane, a mobile harbor crane, a ship's crane or a vehicle boom crane.

* * * * *